(12) United States Patent
Rasor

(10) Patent No.: US 7,645,916 B2
(45) Date of Patent: Jan. 12, 2010

(54) ELASTICALLY DEFORMABLE FABRIC WITH GEL COATED SURFACE

(75) Inventor: Allen C. Rasor, Templeton, CA (US)

(73) Assignee: Specialty Silicone Fabricators, Inc., Paso Robles, CA (US)

( * ) Notice: Subject to any disclaimer, the term of this patent is extended or adjusted under 35 U.S.C. 154(b) by 212 days.

(21) Appl. No.: 11/799,371

(22) Filed: Apr. 30, 2007

(65) Prior Publication Data

US 2007/0207688 A1 Sep. 6, 2007

Related U.S. Application Data

(63) Continuation-in-part of application No. 10/735,015, filed on Dec. 12, 2003, now abandoned.

(60) Provisional application No. 60/442,646, filed on Jan. 23, 2003.

(51) Int. Cl.
*A61F 13/00* (2006.01)

(52) U.S. Cl. .............................. 602/44; 602/41; 442/123

(58) Field of Classification Search ................... 602/41, 602/42, 43, 44, 46, 55, 56, 57, 900; 442/123, 442/149
See application file for complete search history.

(56) References Cited

U.S. PATENT DOCUMENTS

| 4,991,574 | A | 2/1991 | Pocknell | |
|---|---|---|---|---|
| 5,340,363 | A | 8/1994 | Fabo | |
| 6,761,900 | B2 * | 7/2004 | Shudo et al. | 424/448 |
| 2004/0219200 | A1 * | 11/2004 | Shudo et al. | 424/449 |
| 2006/0129081 | A1 * | 6/2006 | Binder et al. | 602/60 |

\* cited by examiner

*Primary Examiner*—Arti Singh-Pandey
(74) *Attorney, Agent, or Firm*—Robert L. McKellar; McKellar IP Law, PLLC

(57) ABSTRACT

An appliqué for the skin for the management of scars that includes an elastically deformable woven fabric having an imperforate, tacky gel coating on one side thereof. The fabric is preferably woven from a thread comprising an elastic polyester or polyether fiber such as LYCRA® or Spandex. The gel coating, which is applied to one side of the fabric, is preferably silicone gel. The appliqué is used for the management of hypertrophic skin conditions.

2 Claims, 2 Drawing Sheets

ELASTICALLY DEFORMABLE FABRIC WITH GEL COATED SURFACE

REFERENCE TO RELATED APPLICATIONS

This application is a continuation in part of U.S. patent application Ser. No. 10/735,015, filed Dec. 12, 2003, which claimed the benefit of U.S. Provisional Application No. 60/442,646, filed Jan. 23, 2003.

BACKGROUND OF THE INVENTION

1. Field of the Invention

The present invention relates to an appliqué consisting of an elastically extensible woven fabric having an imperforate silicone gel coating on one surface thereof which is applied to the skin to overlie a closed wound for the reduction and management of scar tissue formation.

2. Prior Art

Wound dressings are applied directly to wounded or diseased tissue for the absorption of secretion, for protection from trauma, for administration of medicine, to keep the wound clean, or to stop bleeding. Prior art dressings address such issues by providing varying degrees of wound ventilation, of hydrophobic/hydrophyllic capability, and other characteristics depending upon the immediate need. However, the effectiveness of the treatment is sometimes limited by the degree of physical contact between the skin and the dressing itself. Indeed, irregular contours of the body present a challenging topology to customarily flat medical dressings. In the case of pressure dressings, this problem is solved by means of an external wrap. However, the presence of the wrap may interfere with important functions of the dressing, such as its ventilating properties. The location of the wound may also make adequate application of an external wrap impossible.

Spandex was the first manufactured elastic fiber, and was introduced by Dupont under the tradename Lycra® in 1958. Due to its improved strength and ability to hold a dye, spandex replaced extensible fabrics woven from rubber fibers in most garment applications. Spandex fiber is a long-chain synthetic polymer comprised of at least 85% segmented polyurethane. The polymer chain is a segmented block copolymer containing long, randomly coiled, liquid soft segments that move to a more linear, lower entropy structure. The hard segments act as "virtual cross-links" that tie all the polymer chains together into an infinite network. This network prevents the polymer chains from slipping past each other and taking on a permanent set or draw. When the stretching force is removed, the linear, low entropy, soft segments move back to the preferred randomly coiled, higher entropy state, causing the fiber to recover to its original shape and length. The segmented block copolymer is extruded into a fiber comprised of a plurality of coalesced fine filaments. The fibers are woven to provide an extensible fabric. The size and density of the interstices in the fabric depend on the "thread count" and can generally be varied in the weaving process.

Topical dressings such as wound dressings in the form of both perforate and imperforate elastomeric sheets, one side of which has a gel coated thereon, are well known in the art. Nonextensible woven fabrics having one side coated with a gel are also known. Examples of such prior art wound dressings are disclosed in U.S. Pat. Nos. 4,991,574 and 4,838,253. Fabo, in U.S. Pat. No. 5,340,363, discloses a liquid-permeable wound dressing comprising a mesh net of a reinforcing fabric wherein the adjacent fibers defining the interstices of the fabric are impregnated with an elastic hydrophobic gel such as silicone gel but the interstices contain openings to permit fluid to flow through the dressing. Surprisingly, no dressings for topical application have been described wherein the dressing comprises a sheet of fabric woven from elastic fibers and having interstices therein wherein one side of the fabric is coated with an imperforate layer of a hydrophobic gel to occlude the interstice openings and provide a tacky adhesive surface and wherein the opposing surface of the fabric is uncoated and retains the texture and feel of the fabric.

It is generally known in the art that wound dressings preferably be perforate, at least to the passage of air therethrough. Wounds "weep", and a layer of absorbant material normally comprises at least one layer of a wound dressing to absorb the fluid emanating from the wound. The absorbant layer is either in direct contact with the wound of has a fluid-permeable layer of material interposed between the absorbant layer and the wound. After the wound heals, it is desireable to minimize post-traumatic scar formation. The structural considerations required in an appliqué for the management (i.e., the minimization) of scar formation are different than those required in the structure of a wound dressing. For example, it is unnecessary to include an absorbant layer in the appliqué as is the case with wound dressings. Notwithstanding the improvements in wound dressings that have been developed in recent years, there remains a need for an appliqué that may be applied over a healed or closed wound to minimize scar formation.

SUMMARY

It is an object of the present invention to provide an appliqué for adhesion to the skin overlying a healed wound, the appliqué thereafter being operable for minimizing scar formation. The appliqué consists of a sheet of fabric woven from elastically extensible fibers having an imperforate, homogeneous layer of silicone gel coated on a lower, skin-facing surface of the fabric, the upper, opposing surface of the fabric being uncoated.

The features of the invention believed to be novel are set forth with particularity in the appended claims. However the invention itself, both as to organization and method of operation, together with further objects and advantages thereof may be best understood by reference to the following description taken in conjunction with the accompanying drawings.

DESCRIPTION OF THE PREFERRED EMBODIMENTS

Figure 1:
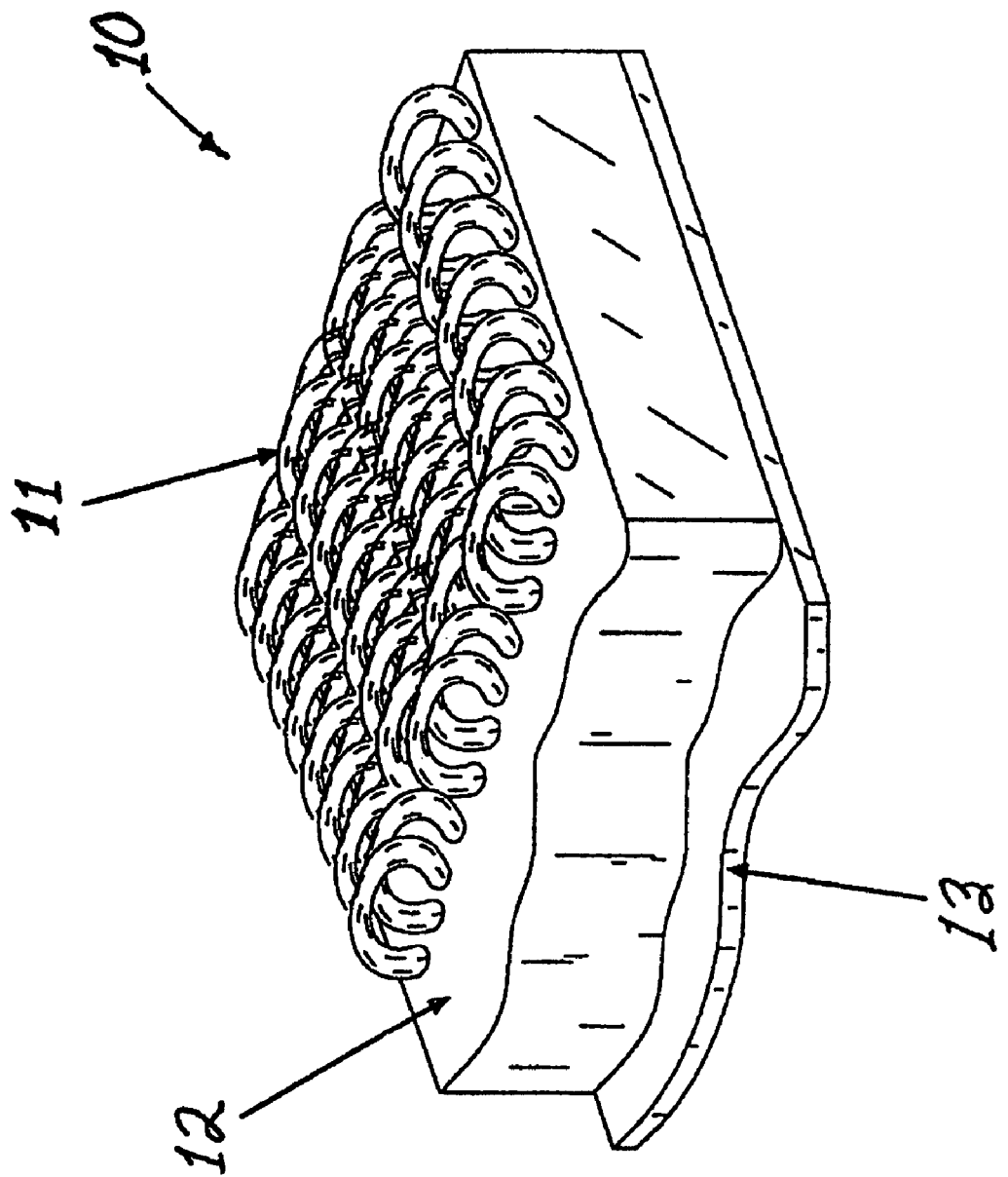
FIG. 1 is a perspective and transverse cross-sectional view of a scar management appliqué in accordance with the present invention.

With reference to FIG. 1, a skin appliqué 10 (i.e., an appliqué adapted for releasable attachment to the skin) consisting of a sheet of elastically extensible fabric 11 having an imperforate layer of a pure, homogeneous silicone gel 12 coated on a lower skin-facing side thereof. The term "elastically extensible fabric", as used herein, means a fabric woven or formed from elastically extensible fibers. A protective release sheet of a suitable releasing material such as polycarbonate film is indicated at numeral 13. The sheet of release material 13 is loosely affixed to a tacky lower skin-contacting surface of the silicone gel layer in opposition to the fabric 11, and is easily separated from the silicone gel layer. The silicone gel layer 12 covering the lower surface of the fabric 11 is continuous, impervious to liquids and is substantially impervious to air because the silicone gel layer 12 does not have apertures therein. The silicone gel layer is forced into (but not through) the interstitial spaces between adjacent fibers in the woven fabric and is firmly affixed to the fabric. The upper surface of the fabric (i.e., the surface of the fabric opposed to the gel-covered surface) remains gel-free and retains the texture of the fabric. The lower skin-contacting surface of the silicone gel layer is tacky and, when the sheet of release material 13 is removed therefrom, provides adhesive means for attaching the scar management appliqué 10 to the surface of the skin bearing the scar tissue. The release layer 13 protects the tacky skin-contacting surface of the silicone gel layer 12 until ready for use and is peeled from the dressing to expose the gel layer 12 prior to use.

Figure 2:
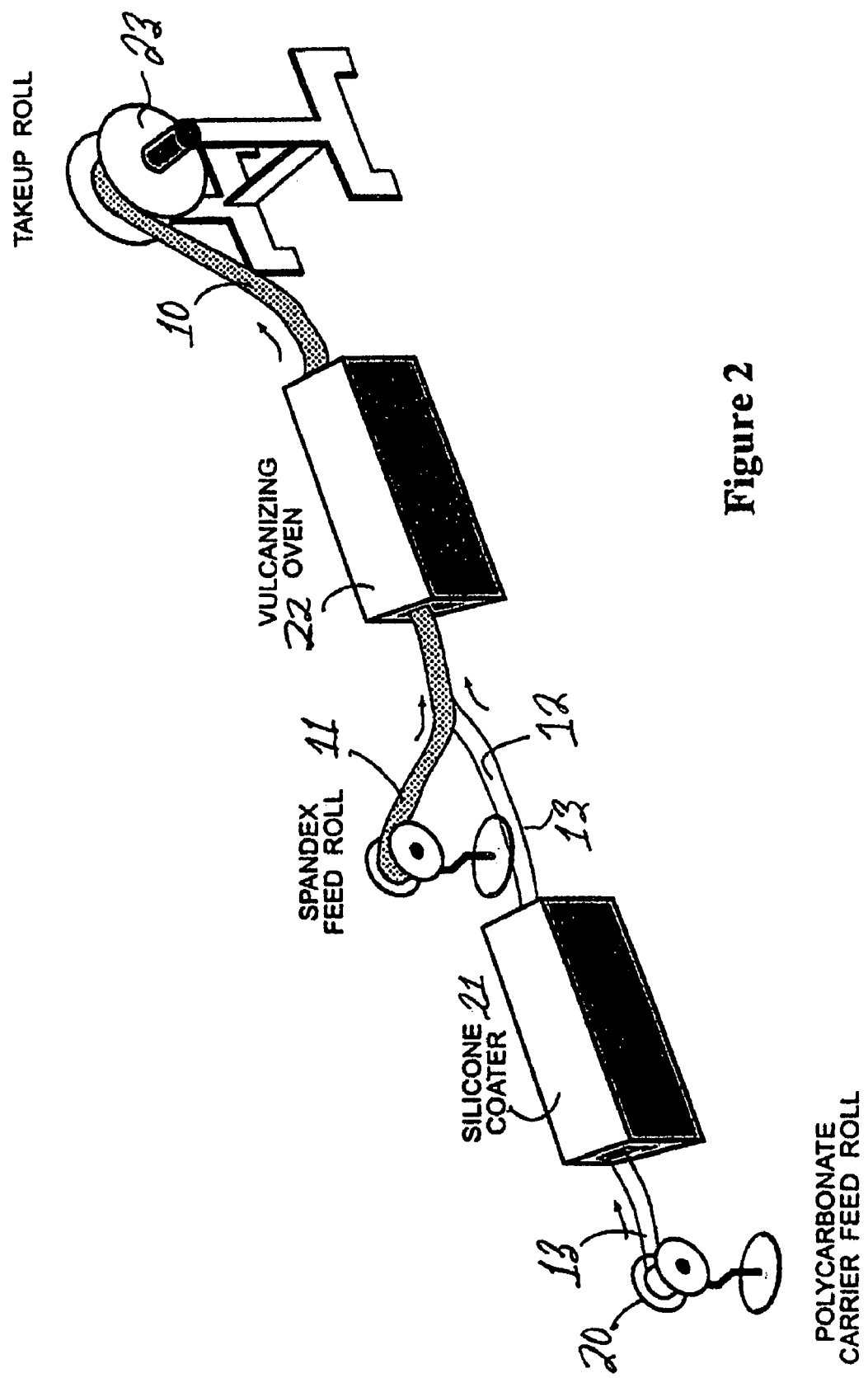
FIG. 2 is a plan view illustrating a process for making a scar management appliqué in accordance with FIG. 1.

Turning now to FIG. 2, a process for fabricating the scar management appliqué 10 is illustrated in plan view. A film of release material 13, such as a polycarbonate sheet, is fed from a bulk roll 20, and brought into and through the gel coating application device 21, wherein the sheet of release material 13 receives a layer of pure, unvulcanized liquid silicone gel 12 having a predetermined thickness. Upon leaving the coating device 21, a sheet of elastically extensible fabric 11 such as Spandex is introduced directly onto the exposed liquid silicone gel surface 12 layered upon the sheet of release material 13 prior to entering the heat-curing oven 22. While passing through the oven 22, the silicone gel component layer 12 is cured, or transformed by the heat into its final viscous gel state. After leaving the oven 22, the bulk, finished product 10 is then rolled onto a take-up reel 23 for storage, secondary bulk cutting, or final shape cutting.

A suitable gel composition for coating the carrier sheet 13 (i.e., the sheet of release material) is available as a 2-part liquid blended in a 1:1 ratio such as MED-6340 (NuSil Technology, Carpinteria, Calif. 93013). MED-6340 is supplied as a Part A and a Part B. The mixture is deaerated under vacuum prior to layering the liquid onto the carrier/release sheet 13. The firmness of the cured silicone gel layer can be increased by increasing the amount of Part B relative to Part A in the mixture. The silicone gel layer is preferably heat-cured (i.e., hot-air vulcanized) by exposure to hot air at a temperature of about 300 degrees F. for 2-3 minutes in the "tunnel" oven 22. It is noted that a variety of curing conditions may be employed. For example, the silicone gel will cure at room temperature given sufficient time.

While particular embodiments of the present invention have been illustrated and described, it would be obvious to those skilled in the art that various other changes and modifications can be made without departing from the spirit and scope of the invention. It is an important feature of the scar management appliqué presented hereinabove that the silicone gel layer is pure and homogeneous. No therapeutic agents are required as additives to the scar-contacting silicone gel layer in order for the appliqué to be operable for its intended scar management function. In addition, the woven fabric may comprise any elastomeric fiber provided that the fiber is elastically deformable. It is another important feature and advantage of the present scar management appliqué that the elastically extensible fabric, together with the cohesive nature of the silicone gel layer coated thereon, enables the dressing to be stretched prior to application to the skin to compress the scar. The compression of the scar during exposure of the scar to the silicone gel layer, enhances the ability of the appliqué to minimize scar formation. The artisan will appreciate that the utility of the appliqué described hereinabove could be extended to non-medical applications such as impact damping inserts for running shoes. It is therefore intended to cover in the appended claims all such changes and modifications that are within the scope of this invention.

What I claim is:

1. A topical appliqué operable for adhesion to the skin adjacent to and overlying a healed wound, the topical appliqué thereafter being operable for mimimizing scar formation, the topical appliqué consisting of: (a) an elastically extensible fabric woven from elastically extensible fibers and having interstitial openings between said fibers, said elastically extensible fabric having an upper surface and a lower skin-facing surface; and (b) an imperforate layer of silicone gel coating said lower skin-facing surface of said elastically extensible fabric.

2. The topical appliqué of claim 1 wherein said imperforate layer of silicone gel has an upper surface affixed to said lower skin-facing surface of said elastically extensible fabric and a lower skin-contacting surface in oposition thereto, said appliqué further comprising a sheet of a release material releasably affixed to said lower skin-contacting surface of said imperforate layer of silicone gel.

* * * * *